United States Patent
Mitchell et al.

(10) Patent No.: US 8,888,978 B2
(45) Date of Patent: Nov. 18, 2014

(54) VENTED OXYGEN CELL

(75) Inventors: Graeme Ramsay Mitchell, Poole (GB); Martin Williamson, Poole (GB); Stuart Harris, Winston (GB)

(73) Assignee: Life Safety Distribution AG, Uster (CH)

(*) Notice: Subject to any disclaimer, the term of this patent is extended or adjusted under 35 U.S.C. 154(b) by 27 days.

(21) Appl. No.: 13/406,574

(22) Filed: Feb. 28, 2012

(65) Prior Publication Data

US 2012/0228139 A1 Sep. 13, 2012

Related U.S. Application Data

(60) Provisional application No. 61/451,778, filed on Mar. 11, 2011.

(51) Int. Cl.
*G01N 27/401* (2006.01)
*G01N 27/404* (2006.01)

(52) U.S. Cl.
CPC .................... *G01N 27/404* (2013.01)
USPC ........................................................ 204/431

(58) Field of Classification Search
USPC ...................... 429/82, 83, 446, 512
See application file for complete search history.

(56) References Cited

U.S. PATENT DOCUMENTS 6,666,963 B1 12/2003 Peng et al.
6,682,844 B2 * 1/2004 Genc ............................. 429/437
7,608,177 B2 * 10/2009 Nauber et al. ................. 204/424
2006/0228597 A1 * 10/2006 Mossman ........................ 429/13
2008/0264975 A1 * 10/2008 Bruder et al. ............... 222/321.3
2009/0036973 A1 * 2/2009 Humphrey et al. ........... 623/1.16
2012/0301563 A1 * 11/2012 Aikens et al. ................. 424/780

FOREIGN PATENT DOCUMENTS

DE 10 2004 059 280 A1 6/2006
EP 2 251 682 A1 11/2010
WO WO 2004/031758 A1 4/2004

OTHER PUBLICATIONS

European Search Report, dated Jul. 2, 2012, corresponding to Application No. EP 12 15 8507.

* cited by examiner

*Primary Examiner* — Jonathan Johnson
*Assistant Examiner* — Kourtney S Carlson
(74) *Attorney, Agent, or Firm* — Husch Blackwell LLP

(57) ABSTRACT

An electrochemical oxygen sensor is provided. The electrochemical sensor includes a housing having first and second compartments, a sensing electrode disposed within the first compartment of the housing, a consumable anode disposed within the second compartment of the housing, a porous separator between the sensing electrode and consumable electrode that separates the first and second compartments and an electrolyte saturating the porous separator and consumable anode. A first aperture on a first end of the housing extends between an outside surface of the housing and first compartment that allows gas access to the sensing electrode. A venting system on a second, opposing end of the housing includes a second aperture extending between the outside surface of the housing and second compartment and has a predetermined permeability that controls pressure in the second compartment and loss of moisture from the sensor.

18 Claims, 3 Drawing Sheets

VENTED OXYGEN CELL

CROSS-REFERENCE TO RELATED APPLICATION

This application claims the benefit of the filing date of U.S. Provisional Application Ser. No. 61/451,778 filed Mar. 11, 2011 entitled, "Vented Oxygen Cell." The '778 application is hereby incorporated herein by reference.

FIELD

The field relates generally to electrochemical sensors and more particularly to oxygen sensors.

BACKGROUND

Electrochemical oxygen sensors are generally known. Such sensors typically rely upon a redox reaction in first and second parts of the sensor. In this case, a precious metal cathode in a first part of the sensor chemically reduces oxygen while a balancing reaction oxidizes a consumable anode (e.g., lead) in a second part of the sensor.

The cathode and consumable anode are coupled through the use of an ionically conducting electrolyte. The second part of the sensor may contain or be filled with the electrolyte. The anode is saturated with this electrolyte.

A fiber separator may separate the first and second parts of the sensor. The fiber separator bounds the second part of the sensor and also becomes saturated with the electrolyte. The separator also contacts the cathode and supports the ionic transfer between the cathode and anode.

During use, oxygen diffuses into the first part of the sensor through an aperture and a gas phase diffusion barrier to react with the cathode. The aperture (capillary) is usually the diffusion controlling element in the design. The membrane shown in the types of sensors considered here is the supporting element for the sensing electrode and is designed not to offer a large diffusion resistance. In this way the sensor performance is controlled by well understood properties of the mechanical capillary rather than the more complex and variable properties of a tape. There is a different style of sensor which uses a solid membrane as the diffusion barrier, through which gas percolates via a form of solid solution process but this has a different type of pressure response.

Vents are more widely known and used for pressure relief in fuel-cell type electrochemical sensors where the drawbacks associated with parasitic consumption of the consumable component is not an issue as is the case for oxygen. In fact, the early attempts to obtain patent coverage on vented oxygen sensors were limited in their technological scope for this reason.

While electrochemical oxygen sensors work well, their operation can become degraded over time. For example, the separator may leak allowing the bulk transfer of gas between the first and second parts of the sensor. In cases where the sensor is subjected to temperature changes, expansion or contraction of gas within the sensor may produce pressure gradients across the separator which can result in bubbles of gas being forced through the separator. When this occurs, gas needs to flow through the capillary of the sensor to compensate for the change in volume due to movement of the bubble(s), which is inconsistent with the principle of diffusion under which the sensor operates. The bulk transport of gas through the first part of the sensor causes the sensor to produce erroneous readings through a process commonly referred to as "glitching." Because of the importance of electrochemical gas sensors, a need exists for methods of providing more reliable sensors.

DETAILED DESCRIPTION OF AN ILLUSTRATED EMBODIMENT

Figure 1:
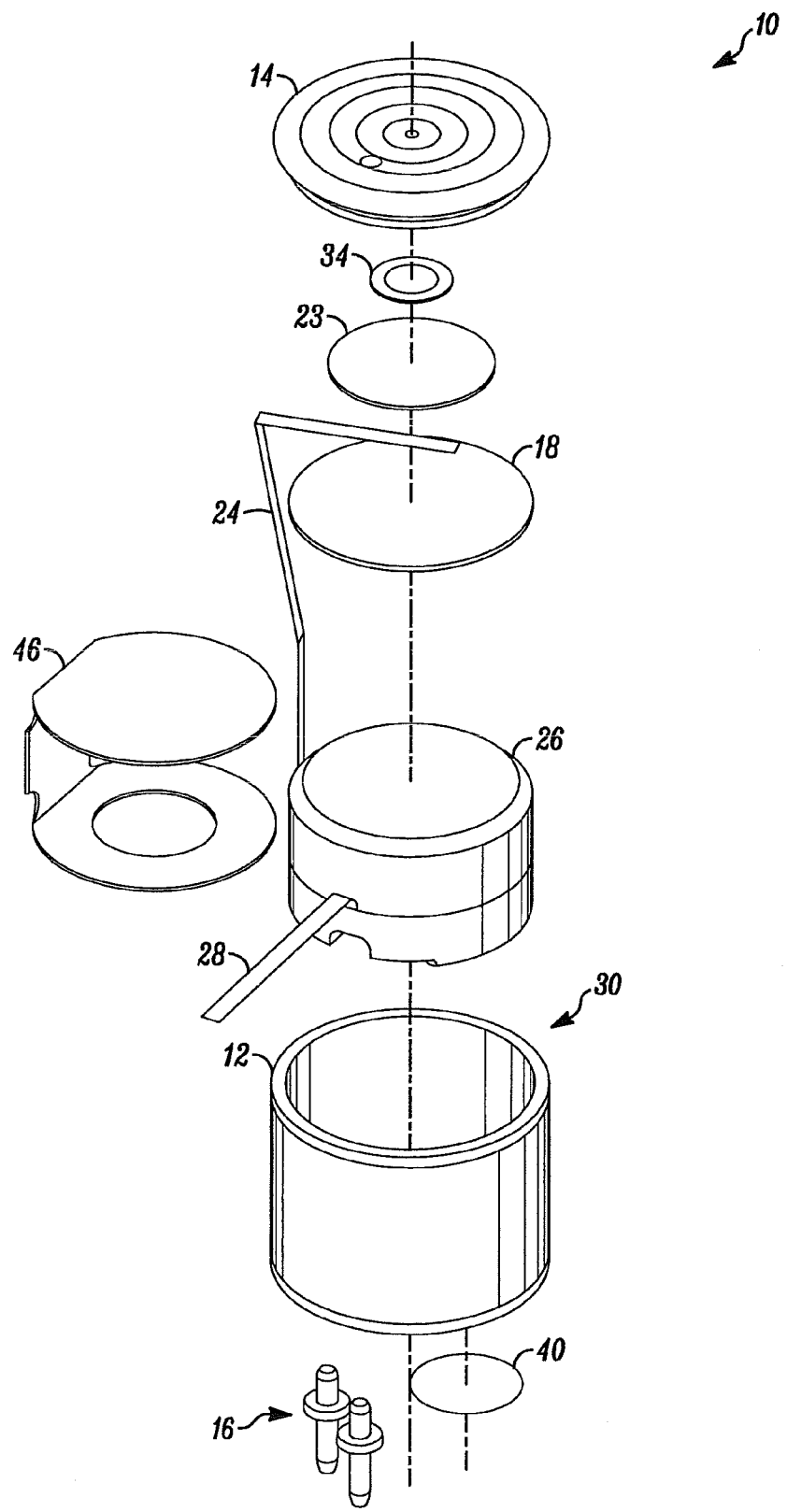
FIG. 1 is a simplified, exploded view of a electrochemical oxygen sensor shown generally in accordance with an illustrated embodiment.

FIG. 1 is an exploded, simplified view of an electrochemical oxygen sensor 10 shown generally in accordance with one illustrated embodiment. The oxygen sensor 10 is generally defined by a housing or body 12 including a cap 14 attached on a first end of the body 12.

A pair of connector pins 16 extend from a second end of the body 12. A signal from the sensor 10 is in the form of a current which flows between the pins when connected to a suitable measuring circuit. The current (from the sensor 10) is measured as a potential difference across a known load, for example.

Figure 2:
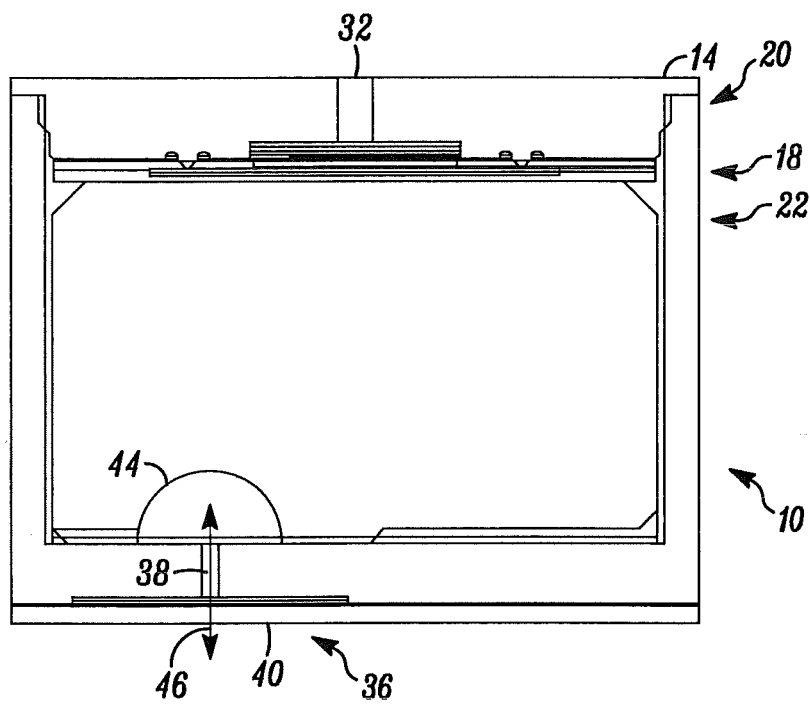
FIG. 2 is a cut-away, further simplified view of the sensor of FIG. 1.

FIG. 2 is a cut-away view of the sensor 10 of FIG. 1 that has been further simplified for purposes of explanation. The body 12 is generally divided into first chamber or compartment 20 and second chamber or compartment 22 by a separator 18. The first compartment 20 is bounded by the cap 14 on a top and the separator 18 on the bottom and by the inside walls of the body 12. Similarly, the second compartment 22 is bounded by the separator 18 on the top and by the bottom of the body 12 by the inside walls of the body 12.

The first compartment 20 includes a noble metal working electrode or cathode 23. A metal current collector 24 electrically connects the cathode 23 with a first one of the connector pins 16. In this case, the collector 24 makes physical and electrical contact with a bottom surface of the cathode 23, extends downward within a slot in the inside walls of the body 12 and electrically connects with the connector pin 16.

The second compartment 22 includes a consumable anode (e.g., a shaped lead wool mass) 26. An anode current collector 28 may extend from and make electrical contact between the anode 26 and the other of the pair of connector pins 16.

The second compartment 22 also includes an electrolyte 30 (e.g., potassium hydroxide or more usually Potassium Acetate) disposed into the body 12 either before assembly of the anode 26 into the body 12 or injected after assembly. The electrolyte 30 is absorbed into the anode 26 and separator 18 and allows a limited amount of free space around the anode 26 and inside walls of the body 12. The free space or volume allows the anode 26 to swell during normal use due to oxidation. The free volume also allows for expansion of the volume of electrolyte 30 during periods of use of the sensor 10 in wet conditions.

Once the sensor 10 has been assembled, the cathode 23, separator 18 and anode 26 are held in close physical contact. The absorption of the electrolyte 30 into the separator 18 allows the electrolyte 30 to form an ionically conducting path between the cathode 23 and anode 26 through the separator 18.

In order to allow oxygen to diffuse into the first compartment 20, a diffusion barrier is provided through the use of a capillary aperture 32 of an appropriate size (e.g., 100 microns) through the cap 14. A diffusion disk 34 (e.g., of a porous PTFE) may be disposed between the aperture 32 and cathode 23 to foster diffusion (spreading) of oxygen across the cathode 23.

As mentioned above, the separator 18 divides the housing into first and second compartments 20, 22. The separator 18 may include one or more layers of a glass fiber or similar material of a relatively small pore size with good wicking properties that draw the electrolyte 30 into the separator 18.

Since the separator 18 has a significantly lower pore size than the lead wool mass of the anode 26, the separator 18 will become completely flooded with electrolyte 20 and therefore produce a relatively good, impervious seal between the first and second compartments 20, 22. However, if the pressure difference between the first and second compartments should exceed a bubble pressure of the separator 18, then a leak will develop between the first and second compartments 20, 22 resulting in the mass flow of gas between the first and second compartments 20, 22.

This mass flow of gas between the first and second compartments results in a flow of oxygen across the cathode 23 that is much greater than would otherwise be produced by diffusion. The result is the significant reading error referred to above as a glitch. Glitches are especially present whenever the sensor 10 is subjected to rapid temperature changes, such as being taken from a hot to a cold area or visa versa.

In order to reduce the possibility of glitches, the sensor 10 is provided with a vent system 36 on a side of the body 12 that is opposite the diffusion aperture 32. Opposite in this case means on an opposite side of the separator. Alternatively, the (one or more) vents might be situated in the side wall of the sensor. In general, the vent could be anywhere in the body, in fact ideally it should come out of the top of the sensor so that both the vent and capillary are exposed to the same ambient pressure rather than the vent being inside the instrument and the capillary outside the instrument. In this regard, the size and features of the vent system 36 may be chosen to minimize the possibility of exceeding the bubble pressure of the separator 18.

For example, the vent system 36 includes an aperture 38 of a size and length that may operate alone or in conjunction with a vent covering membrane to balance the pressure across the separator 18. In this regard, the aperture 38 may be chosen with a diameter of from 5 to 60 microns and a length that could vary in the application from 1.0 to 2.5 mm. Alternatively, as opposed to the way shown in the drawings, it may be beneficial to have a vent that runs from the base up to the top of the sensor through a suitable "pipe." Vents with apertures having a diameter of greater than 60 microns can lead to performance issues particularly when the sensor 10 is operated in hot dry conditions due to water loss, or due to oxygen access from the vent resulting in, for example, a high background current.

In general, it should be emphasized that the vent/covering membrane combination need to provide sufficient gas access (i.e., have sufficient combined porosity) to allow the required speed of bulk flow to mitigate pressure differentials generated by environmental changes within the specified range. There are clearly problems that could be associated with the porosity being too low (i.e., the vent cannot cope with large differentials) whereas if the porosity to too great, the pressure equalisation works well but at the cost of much greater parasitic consumption of lead and other undesirable effects as has been noted. The permeability of the membrane over the vent is not designed on its own to act as the controlling element. That is, it works in combination with the vent and the pair are tuned to meet the needs of the particular sensor design.

The optimum combination will vary depending on the remainder of the cell design. The vent system 36 may be provided with a sealed, porous membrane (e.g., PTFE) 40 (FIG. 1) that covers the aperture 38. In this regard, the porous membrane 40 may be chosen with a predetermined permeability somewhere in the range of 2000 to 6000 Gurley seconds. The use of a predetermined permeability controls pressure within the second compartment and also prevents the transmission or diffusion of water vapor or electrolyte 30 out of the sensor and as a means of controlling moisture loss from the sensor 10. In practice, the PTFE membrane may have negligible restriction of water vapor diffusion, but will prevent liquid leakage.

Figure 3:
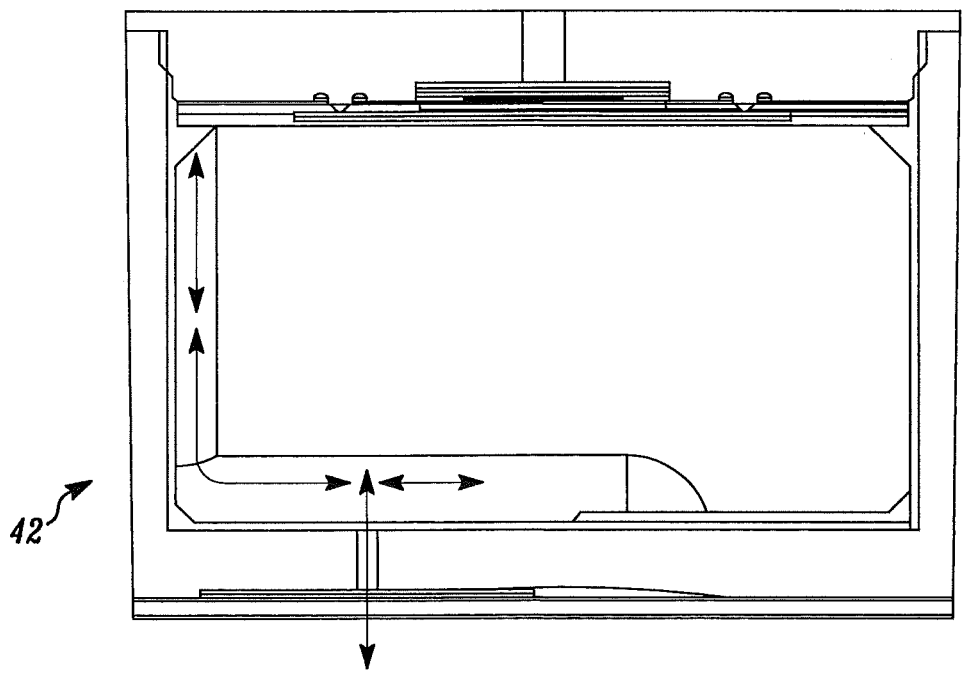
FIG. 3 is a cut-away, simplified view of the sensor of FIG. 1 under another illustrated embodiment.

In order to further control pressure across the separator 18, the vent system 36 may also include one or more channels within the second compartment located between an inside wall of the housing 12 and anode 26 and extending from the vent aperture 38 upwards towards the first chamber 20. In this regard, FIG. 3 shows an example of a channel 42 extending across a bottom of the body 12 and up the sidewall towards the separator 18.

Figure 4:
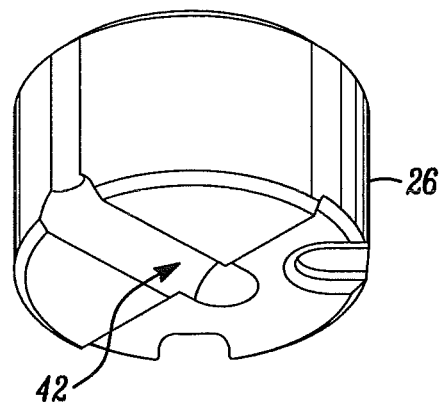
FIG. 4 is a side perspective view of the anode of FIG. 1.

In general, the channels 42 may be created in the inside walls of the body 12, on the outside surface of the anode 26, or both. In this regard, FIG. 4 shows the channels 42 created or otherwise defined by one or more grooves on the outside surface of the anode 26.

Figure 5:
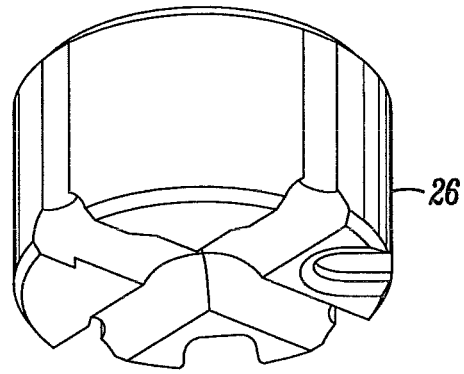
FIG. 5 is a side perspective view of the anode of FIG. 1 under another embodiment.

FIG. 5 shows another illustrated embodiment. In the case of FIG. 5, a set of channels 42 may be created at right angles to one another across a bottom of the anode 26 extending to the sidewalls of the body 12 and then upwards towards the separator 18. In either case of FIG. 4 or 5, a dome 44 may be created in the anode 26 directly adjacent the vent aperture 38 to facilitate entry of gas 46 into the sensor 10 during overpressure conditions.

Figure 6:
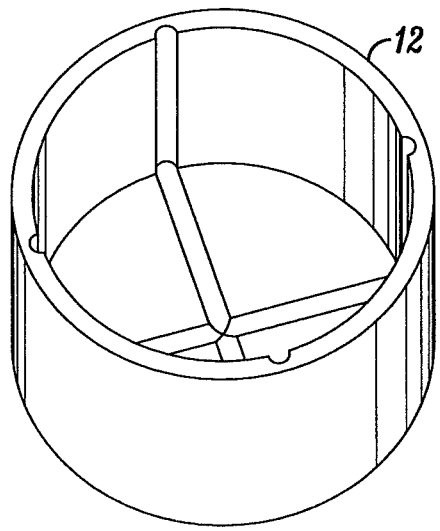
FIG. 6 is a side perspective view of the body of FIG. 1 under an illustrated embodiment.

FIG. 6 shows one or more channels 42 created or otherwise defined by one or more grooves on the inside wall of the body 12. As above, the channels 42 may extend across the bottom of the body 12 and up the sidewalls towards the separator.

In still another embodiment, the separator 18 of FIG. 1 may be provided with an additional capillary layer 46, a first part of which is coextensive with the separator 18 and a second part of which extends outwards from the separator 18 down a sidewall of the body 12 between the sidewall and anode 26 and across the bottom of the anode 26. An aperture may be provided in the bottom portion of the capillary layer 46 to accommodate the dome 44 of FIG. 2.

The capillary layer 46 functions to attract and draw electrolyte 30 away from the vent system 36. This not only ensures that the channels 42 remain unobstructed, but also operates to wick additional electrolyte 30 back to the interface between the cathode 23 and anode 26 in order to ensure sensor reliability even in cases where the sensor 10 begins to loose moisture from the electrolyte 30.

A feature of one of the illustrated embodiments includes an electrochemical oxygen sensor. The electrochemical sensor includes a housing having first and second compartments, a sensing electrode disposed within the first compartment of the housing, a consumable anode disposed within the second compartment of the housing, a porous separator between the sensing electrode and consumable electrode that separates the first and second compartments, an electrolyte saturating the porous separator and consumable anode, a first aperture on a first end of the housing extending between an outside surface of the housing and first compartment that allows gas access to the sensing electrode and a venting system on a second, opposing end side wall case of the housing including a second aperture extending between the outside surface of the housing and second compartment and having a predetermined permeability that controls pressure in the second compartment and loss of moisture from the sensor.

A further feature of the embodiment includes the context where the venting system further includes a gas permeable, liquid impermeable membrane covering the second aperture.

A further feature of the embodiment includes a channel within the second chamber located between an inside wall of the housing and consumable counter electrode and extending from the second aperture towards the first chamber.

A further feature of the embodiment includes the sensor wherein the predetermined permeability has a range of 2000 to 6000 Gurley seconds.

A further feature of the embodiment includes the sensor wherein the second aperture further comprises a diameter of 15 to 60 microns.

A further feature includes the sensor wherein the first aperture further comprises a diameter of 100 microns.

A further feature includes the sensor wherein the separator further comprises a capillary layer that wicks or otherwise draws electrolyte from an area of the venting system to an area of the separator.

In another embodiment, a feature includes an electrochemical oxygen sensor including a housing having first and second compartments, a sensing electrode disposed within the first compartment of the housing, a consumable anode disposed within the second compartment of the housing, a porous separator between the sensing electrode and consumable electrode that separates the first and second compartments, an electrolyte saturating the porous separator and consumable anode, a first aperture on a first end of the housing extending between an outside surface of the housing and first compartment that allows gas access to the sensing electrode, a second aperture on a second, opposing end of the housing extending between the outside surface of the housing and second compartment, a gas permeable, liquid impermeable membrane covering the second aperture and a channel within the second chamber located between an inside wall of the housing and consumable counter electrode and extending from the second aperture towards the first chamber.

A further feature includes the sensor wherein the gas permeable, liquid impermeable membrane covering the second aperture further comprises a permeability of 2000 to 6000 Gurley seconds.

A further feature includes the sensor wherein the second aperture further comprises a diameter of 15 to 60 microns.

A further feature includes the sensor wherein the channel is defined on the inner surface of the housing.

A further feature includes the sensor wherein the channel further comprises a cross-sectional area of at least 0.5 mm².

A further feature includes the context where the channel is defined in an outer surface of the consumable anode.

A further feature includes the sensor wherein the channel further includes a plurality of channels within the second chamber each located between an inside wall of the housing and consumable counter electrode and each extending from the second aperture towards the first chamber.

A further feature includes the sensor with a dome defined in the outer surface of the consumable anode directly adjacent the second aperture.

A further feature includes the sensor with a fibrous material extending between the separator and second aperture that wicks the electrolyte away from the second aperture.

In still another embodiment, the sensor includes a housing having first and second compartments, a sensing electrode disposed within the first compartment of the housing, a consumable anode disposed within the second compartment of the housing, a porous separator between the sensing electrode and consumable electrode that separates the first and second compartments, an electrolyte saturating the porous separator and consumable anode, a first aperture on a first end of the housing extending between an outside surface of the housing and first compartment that allows gas access to the sensing electrode, a second aperture having a diameter of 15 to 60 microns on a second, opposing end of the housing extending between the outside surface of the housing and second compartment, a gas permeable, liquid impermeable membrane having a permeability of 2000 to 600 Gurley seconds covering the second aperture and a channel within the second chamber located between an inside wall of the housing and consumable counter electrode and extending from the second aperture towards the first chamber.

A further feature of the embodiment includes the sensor wherein the channel further comprises a plurality of channels.

A further feature includes the sensor wherein the plurality of channels further comprises a dome in a bottom surface of the anode over the second apertures with the plurality of channels extending outwards from the dome.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. An apparatus comprising:
   an electrochemical oxygen sensor, the electrochemical sensor further comprising:
      a housing having first and second compartments;
      a sensing electrode disposed within the first compartment of the housing;
      a consumable anode disposed within the second compartment of the housing;
      a porous separator between the sensing electrode and consumable anode that separates the first and second compartments;
      an electrolyte saturating the porous separator and consumable anode;
      a first aperture on a first end of the housing extending between an outside surface of the housing and first compartment that allows gas access to the sensing electrode; and
      a venting system on a second, opposing end of the housing including a second aperture extending between the outside surface of the housing and second compartment and having a predetermined permeability that controls pressure in the second compartment and loss of moisture from the sensor, wherein the predetermined permeability further comprises a range of 2000 to 6000 Gurley seconds.

2. The apparatus as in claim 1 wherein the venting system further comprises a gas permeable, liquid impermeable membrane covering the second aperture.

3. The apparatus as in claim 1 further comprising a channel within the second chamber located between an inside wall of the housing and consumable anode and extending from the second aperture towards the first chamber.

4. The apparatus as in claim 1 wherein the second aperture further comprises a diameter of 15 to 60 microns.

5. The apparatus as in claim 1 wherein the first aperture further comprises a diameter of 100 microns.

6. The apparatus as in claim 1 wherein the separator further comprises a capillary layer that wicks or otherwise draws electrolyte from an area of the venting system to an area of the separator.

7. An apparatus comprising:
   an electrochemical oxygen sensor further comprising:
   a housing having first and second compartments;
   a sensing electrode disposed within the first compartment of the housing;
   a consumable anode disposed within the second compartment of the housing;
   a porous separator between the sensing electrode and consumable anode that separates the first and second compartments;
   an electrolyte saturating the porous separator and consumable anode;
   a first aperture on a first end of the housing extending between an outside surface of the housing and first compartment that allows gas access to the sensing electrode;
   a second aperture on a second, opposing end of the housing extending between the outside surface of the housing and second compaitment;
   a gas permeable, liquid impermeable membrane covering the second aperture, the gas permeable, liquid impermeable membrane and second aperture having a predetermined level of permeability that controls gas pressure in the second compartment and loss of moisture from the second compartment, wherein the predetermined permeability is defined in part by a diameter and length of the second aperture; and
   a channel within the second chamber located between an inside wall of the housing and consumable anode and extending from the second aperture towards the first chamber wherein the predetermined permeability further comprises a range of 2000 to 6000 Gurley seconds.

8. The apparatus as in claim 7 wherein the second aperture further comprises a diameter of 15 to 60 microns.

9. The apparatus as in claim 7 wherein the channel is defined by a groove located on the inner surface of the housing.

10. The apparatus as in claim 7 wherein the channel further comprises a cross-sectional area of at least 0.5 mm$^2$.

11. The apparatus as in claim 7 wherein the channel is defined by a groove on an outer surface of the consumable anode.

12. The apparatus as in claim 7 wherein the channel further includes a plurality of channels within the second chamber each located between an inside wall of the housing and consumable anode and each extending from the second aperture towards the first chamber.

13. The apparatus as in claim 7 further comprising a dome defined in the outer surface of the consumable anode directly adjacent the second aperture.

14. The apparatus as in claim 7 further comprising a fibrous material extending between the separator and second aperture that wicks the electrolyte away from the second aperture.

15. An apparatus comprising:
   an electrochemical sensor comprising:
   a housing having first and second compartments;
   a sensing electrode disposed within the first compartment of the housing;
   a consumable anode disposed within the second compartment of the housing;
   a porous separator between the sensing electrode and consumable anode that separates the first and second compartments;
   an electrolyte saturating the porous separator and consumable anode;
   a first aperture on a first end of the housing extending between an outside surface of the housing and first compartment that allows gas access to the sensing electrode;
   a second aperture having a diameter of 15 to 60 microns on a second, opposing end of the housing extending between the outside surface of the housing and second compartment;
   a gas permeable, liquid impermeable membrane having a permeability of 2000 to 6000 Gurley seconds covering the second aperture; and
   a channel within the second chamber located between an inside wall of the housing and consumable anode and extending from the second aperture towards the first chamber.

16. The apparatus as in claim 15 wherein the channel further comprises a plurality of channels.

17. The apparatus as in claim 15 wherein the plurality of channels further comprises a dome in a bottom surface of the anode over the second apertures with the plurality of channels extending outwards from the dome.

18. The apparatus as in claim 15 further comprising a fibrous material extending between the separator and second aperture that wicks the electrolyte away from the second aperture.

* * * * *